(12) United States Patent
Park et al.

(10) Patent No.: US 7,012,144 B2
(45) Date of Patent: Mar. 14, 2006

(54) QUINOLONE CARBOXYLIC ACID DERIVATIVES

(75) Inventors: Tae-Ho Park, Daejeon (KR); Sang-Ho Lee, Daejeon (KR); Cheol Han, Daejeon (KR)

(73) Assignee: Korea Research Institute of Chemical Technology, (KR)

(*) Notice: Subject to any disclaimer, the term of this patent is extended or adjusted under 35 U.S.C. 154(b) by 0 days.

(21) Appl. No.: 10/331,457

(22) Filed: Dec. 27, 2002

(65) Prior Publication Data

US 2003/0130302 A1 Jul. 10, 2003

(30) Foreign Application Priority Data

Dec. 31, 2001 (KR) .................. 10-2001-0088822
Dec. 31, 2001 (KR) .................. 10-2001-0088829

(51) Int. Cl.
*C07D 471/04* (2006.01)
*C07D 401/04* (2006.01)

(52) U.S. Cl. .................. 546/123; 546/110; 546/156; 540/586

(58) Field of Classification Search ............... 546/156, 546/123, 110; 540/586
See application file for complete search history.

(56) References Cited

U.S. PATENT DOCUMENTS

| | | | |
|---|---|---|---|
| 5,221,676 A | * | 6/1993 | Laborde et al. ............. 514/300 |
| 6,762,181 B1 | * | 7/2004 | Takemura et al. ....... 514/230.2 |
| 2003/0232818 A1 | * | 12/2003 | Anderson et al. ........ 514/228.2 |

* cited by examiner

Primary Examiner—Patricia L. Morris
(74) Attorney, Agent, or Firm—Anderson Kill & Olick, P.C.

(57) ABSTRACT

Quinolone carboxylic acid derivatives of formula (I) and pharmaceutically acceptable salts thereof have potent antibacterial activity:

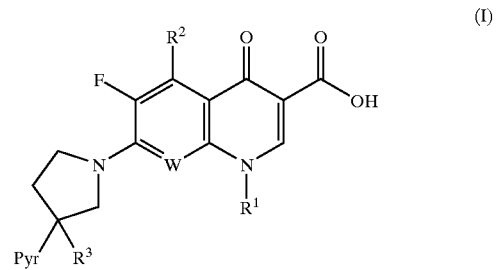

(I)

wherein, $R^1$ is a $C_{1-4}$ alkyl group, or phenyl or $C_{3-6}$ cycloalkyl group optionally substituted with one or more halogens;

$R^2$ is H, amino or $C_{1-4}$ alkyl group;

$R^3$ is H, $C_{1-4}$ alkyl group, or amino, aminomethyl or aminoethyl group optionally substituted with one $C_{1-4}$ alkyl radical;

W is N, CH or CY (Y is halogen, or $C_{1-4}$ alkyl or $C_{1-4}$ alkoxy group optionally substituted with one or more halogens); and Pyr represents 2-, 3- or 4-pyridyl group, provided that when W is C, W and $R^1$ are fused together to form $COCH_2CH(CH_3)$, $CCH_2CH_2CH(CH_3)$, or $CSCH_2CH(CH_3)$.

2 Claims, No Drawings

QUINOLONE CARBOXYLIC ACID DERIVATIVES

FIELD OF THE INVENTION

The present invention relates to novel quinolone carboxylic acid derivatives and pharmaceutically acceptable salts thereof having an excellent antibacterial activity, a process for preparing the same, and an antibacterial composition containing the same as an active ingredient.

BACKGROUND OF THE INVENTION

Many quinolone derivatives are known to exhibit high antibacterial activities(see U.S. Pat. Nos. 4,670,444, 4,795,751 and 5,631,266). However, some of the conventional quinolone compounds have limited activities against Gram-positive bacteria, while other quinolone derivatives exhibit the problem of poor water-solubility and bioavailability or side effects such as high cytotoxicity.

The present inventors have, therefore, endeavored to develop non-toxic compounds having the higher potency against the broad spectrum of bacteria; and have unexpectedly found that certain quinolone carboxylic acid derivatives having a pyridylpyrrolidine moiety at the 7-position of the quinolone nucleus exhibit the broad spectrum antibacterial activity and the reduced cytotoxicity.

SUMMARY OF THE INVENTION

It is, therefore, a primary object of the present invention to provide novel quinolone carboxylic acid derivatives, pharmaceutically acceptable salts thereof, having the potent antibacterial activity and low cytotoxicity.

It is another object of the present invention to provide an antibacterial composition containing the inventive compound as an active ingredient.

It is a further object of the present invention to provide a process for the preparation of the inventive novel compound.

In accordance with one aspect of the present invention, there is provided a quinolone carboxylic acid derivative of formula (I) or a pharmaceutically acceptable salt thereof:

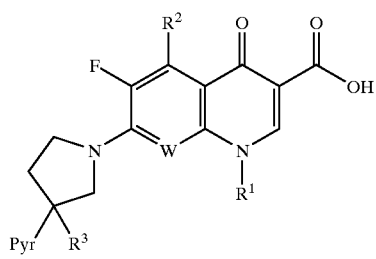

(I)

wherein
$R^1$ is $C_{1-4}$ alkyl group, or phenyl or $C_{3-6}$ cycloalkyl group optionally substituted with one or more halogens;
$R^2$ is H, amino or $C_{1-4}$ alkyl group;
$R^3$ is H, $C_{1-4}$ alkyl group, or amino, aminomethyl or aminoethyl group optionally substituted with one $C_{1-4}$ alkyl radical;
W is N, CH or CY (Y is halogen, or $C_{1-4}$ alkyl or $C_{1-4}$ alkoxy group optionally substituted with one or more halogens); and Pyr represents 2-, 3- or 4-pyridyl group, provided that when W is C, W and $R^1$ are fused together to form $COCH_2CH(CH_3)$, $CCH_2CH_2CH(CH_3)$, or $CSCH_2CH(CH_3)$.

In accordance with another aspect of the present invention, there is provided a process for preparing a quinolone carboxylic acid derivative of formula (I) or a pharmaceutically acceptable salt thereof, which comprises reacting a compound of formula (II) with a compound of formula (III) in the presence of a base:

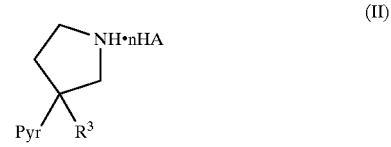

(II)

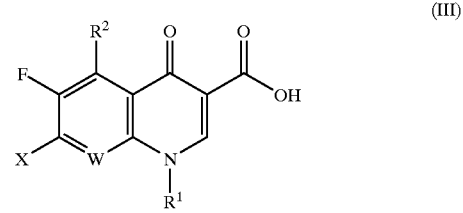

(III)

wherein
$R^1$, $R^2$, $R^3$, W and Pyr are as defined above;
n is 0, 2 or 3;
X represents halogen atom; and
HA represents hydrogen chloride or trifluoroacetic acid.

In accordance with a further aspect of the present invention, there is provided an antibacterial composition comprising an effective amount of the quinolone carboxylic acid derivative of formula (I) or a pharmaceutically acceptable salt thereof as an active ingredient, and a pharmaceutically acceptable carrier and/or adjuvant.

DETAILED DESCRIPTION OF THE INVENTION

Among the compounds of the present invention, preferred are those wherein: $R^1$ is ethyl, t-butyl, cyclopropyl, 2,4-difluorophenyl or 2-(S)-fluorocyclopropyl group; $R^2$ is hydrogen, amino or methyl group; $R^3$ is hydrogen, methyl, amino, methylamino, aminomethyl, methylaminomethyl or 1-aminoethyl group; W is N, CH, CF, CCl, $CCH_3$, $COCH_3$, $COCH_2F$ or $COCHF_2$ group; Pyr is 2-, 3- or 4-pyridyl group; and W and $R^1$ together form $COCH_2CH(CH_3)$, $CCH_2CH_2CH(CH_3)$, or $CSCH_2CH(CH_3)$.

The pharmaceutically acceptable non-toxic salts of the compounds of formula (I) which fall within the scope of the present invention include salts of amino group formed with inorganic acids such as hydrochloric acid, sulfuric acid, phosphoric acid and nitric acid, or with organic acids such as tartaric acid, fumaric acid, citric acid, methanesulfonic acid, oxalic acid and acetic acid.

The pharmaceutically acceptable salt of the present invention may be prepared in accordance with a known method, e.g., by reacting the compound of formula (I) with a suitable acid in the presence of a solvent, e.g., methanol, ethanol, dichloromethane, ethyl acetate or diethyl ether.

The compound of formula (I) may be prepared by a process which comprises reacting a compound of formula (II) with a compound of formula (III) in the presence of a base:

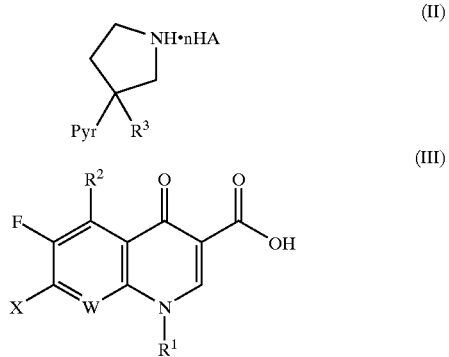

wherein, $R^1$, $R^2$, $R^3$, W, X, n, HA and Pyr are as defined above.

The condensation reaction of the compounds of formulas (II) and (III) may be conducted at a temperature ranging from 20 to 120□ for a period from 6 to 14 hours in water or an organic solvent. Exemplary solvents which may be suitably used in the process of the present invention include acetonitrile, dimethylformamide, dimethylsulfoxide and pyridine. It is desirable to carry out the coupling reaction between compound of formula (II) and compound of formula (III) at molar ratio of 1 to 1.5 moles of compound of formula (II) per mole of compound of formula (III), in the presence of inorganic acid-acceptor such as $CaCO_3$ and $NaHCO_3$ or organic acid-acceptor such as triethylamine, pyridine, diazabicyclo[5.4.0]undec-7-ene and diisopropylethylamine at molar ratio of 1 to 10 moles of acid acceptor per mole of compound of formula (III).

The compound of formula (III) may be prepared in accordance with a known method(see Chem. Pharm. Bull., 34, 4098(1986); J. Hetero., Chem., 24, 181; J. Med. Chem., 31, 503(1988); European Patent Publication No. 115,841; and Japanese Laid-open Patent Publication No. 62-252772), or may be commercially available.

Further, the compound of formula (II) may be prepared by a method disclosed in Korea Patent Application No. 2001-88829 filed on Dec. 31, 2001.

Specifically, at first, when $R^3$ is hydrogen or an alkyl group, the compound of formula (II) can be prepared by reacting a trialkylphosphonoacetate with an acetylpyridine derivative or a formylpyridine derivative, followed by conducting the Wittig reaction, the nitromethylation, the hydrogenation, the reduction of carbonyl group, the protection and deprotection of amino group.

Further, when $R^3$ is aminomethyl or aminoethyl group, the compound of formula (II) can be prepared by alkylating a cyanomethylpyridine derivative to provide a nitrile derivative, followed by the chloromethylation, the azidation, the deprotection of hydroxy group, the reaction with triphenyl phosphine, the protection of amino group, the reduction, the protection of amino group, the alkylation, the deprotection of amino groups of the prrolidine derivative, or followed by the alkylation with bromoacetate to give an ester derivative, the hydrolysis, the protection of amino group, the oxidation, the deprotection of hydroxy group, the mesylation, the reduction, the protection of amino group, and deprotection of amino groups of the ester derivative.

Furthermore, when $R^3$ is amino, the compound of formula (II) can be prepared by converting a nitrile derivative of pyridine to a carbamoyl derivative, followed by the rearrangement of carbamoyl group, the alkylation and the deprotection of the carbamate derivative. of pyrrolidine The compounds of the present invention may be administered, either orally or intraperitoneally, in an effective amount ranging from 2.5 mg/kg to 100 mg/kg, preferably from 5 mg/kg to 60 mg/kg to a subject patient per day.

The present invention also includes within its scope an antibacterial composition comprising one or more of the inventive compounds as an active ingredient.

The pharmaceutical compositions of the invention may be formulated for administration orally or by injection. The composition for oral administration may take various forms such as tablets and gelatin capsules, which may contain conventional additives such as a diluent (e.g., lactose, dextrose, sucrose, mannitol, sorbitol, cellulose and/or glycine), a lubricant (e.g., silica, talc, stearic acid or its magnesium and calcium salts and polyethylene glycol). In the case of the tablet form, the composition may further comprise a binder (e.g., magnesium aluminum silicate, starch paste, gelatin, tragacanth, methyl cellulose, sodium carboxymethyl cellulose and polyvinyl picolidine) and optionally a disintegrant (e.g., starch, agar and alginic acid or its sodium salt), absorbent, colorant, flavor, sweetener and the like. The composition for injection may be an isotonic solution or a suspension.

The composition may be sterilized and/or contain an adjuvant such as a preservative, stabilizer, wetting agent, emulsifier, a salt for controlling an osmotic pressure and/or a buffer solution, and other pharmaceutically effective materials.

The pharmaceutical compositions can be prepared by a conventional mixing, granulating or coating method and may contain preferably about 0.1 to 75%, more preferably about 1 to 50% of the active ingredient of this invention.

The following Preparation and Examples are given for the purpose of illustration only and are not intended to limit the scope of the invention.

In the Preparation and Examples, unless otherwise specified, the evaporation was conducted under a reduced pressure, preferably under a pressure ranging from about 15 to 100 mmHg.

Preparation 1: Synthesis of 3-aminomethyl-3-(pyridin-2-yl) pyrrolidine trihydrochloride Step 1) Synthesis of 2-(Pyridin-2-yl)-4-(tetrahydropyran-2-yloxy)butyro-nitrile To 230 ml of tetrahydrofuran (THF) was added 10 g of (pyridyl-2-yl)acetonitrile, and the resulting mixture was stirred sufficiently at −78° C. under nitrogen gas blanket. Then, 46.5 ml of 2M lithium diisopropylamide solution was slowly added and the resulting mixture was stirred for 1 hour and thereto was slowly added a solution of 21.2 g of 2-(2-bromoethoxy)tetrahydropyran in 20 ml of THF. After one hour, the resulting mixture was stirred at room temperature for four hours. After the reaction was completed, an aqueous ammonium chloride solution was added, the reaction mixture was extracted with ethyl acetate. The organic phase was dried over anhydrous magnesium sulfate and concentrated under reduced pressure, and the residue thus obtained was purified by a silica gel column chromatography using a mixture of ethyl acetate and n-hexane of 1:4 to obtain 13.2 g of the title compound as an oil.

$^1$H NMR(200 MHz, CDCl$_3$) δ8.6 (1H, m), 7.7 (1H, m), 7.6 (1H, m), 7.2 (1H, m), 4.6 (1H, m), 4.2 (1H, m), 3.9 (2H, m), 3.6 (2H, m), 2.3 (2H, m), 1.6 (6H, m)

Step 2) Synthesis of 2-chloromethyl-2-(pyridin-2-yl)-4-(tetrahydropyran-2-yloxy)butyronitrile A solution of 20 g of the compound obtained in Step 1 in 400 ml of THF was stirred at −78° C. under atmosphere of nitrogen, and then, 45 ml of 2M lithium diisopropylamide solution was slowly added thereto. The resulting mixture was stirred for one hour and thereto was slowly added a solution of 13.62 g of bromochloromethane in 30 ml of THF. After one hour, the resulting mixture was stirred at room temperature for four hours. After the reaction was completed, an aqueous ammonium chloride solution was added, the reaction mixture was extracted with ethyl acetate. The organic phase was dried over anhydrous magnesium sulfate and concentrated under reduced pressure, and the residue thus obtained was purified by a silica gel column chromatography using a mixture of ethyl acetate and n-hexane of 1:6 to obtain 19.14 g of the title compound as an oil.

$^1$H NMR(300 MHz, CDCl$_3$) δ8.6 (1H, m), 7.7 (1H, m), 7.3 (1H, m), 4.5 (1H, m), 4.1 (2H, m), 3.8 (2H, m), 3.4 (2H, m), 2.5 (2H, m), 1.6 (6H, m)

Step 3) Synthesis of 2-azidomethyl-2-(pyridin-2-yl)-4-(tetrahydropyran-2-yloxy)butyronitrile To a solution of 8.01 g of the compound obtained in Step 2 in 200 ml of dimethylformamide(DMF) was added 8.84 g of sodium azide. The resulting mixture was stirred for 18 hours at 140° C. After the reaction was completed, water was added, and the reaction mixture was extracted with ethyl acetate. The organic phase was dried over anhydrous magnesium sulfate and concentrated under reduced pressure, and the residue thus obtained was purified by a silica gel column chromatography using a mixture of ethyl acetate and n-hexane of 1:6 to obtain 6.2 g of the title compound as an oil.

$^1$H NMR(200 MHz, CDCl$_3$) δ8.6 (1H, m), 7.7 (1H, m), 7.3 (1H, m), 4.5 (1H, m), 4.1~3.6 (4H, m), 3.4 (2H, m), 3.4 (2H, m), 2.5 (2H, m), 1.6 (6H, m)

Step 4) Synthesis of 2-azidomethyl-2-(pyridin-2-yl)-4-hydroxybutyronitrile

To a solution of 4.72 g of the compound obtained in Step 3 in 100 ml of methanol was added 40 ml of IN HCl solution, and the resulting mixture was stirred for 6 hours. After the reaction was completed, the reaction solution was neutralized with sodium hydrogen carbonate solution, distilled under reduced pressure to remove methanol therefrom, and extracted with ethyl acetate. The organic phase was dried over anhydrous magnesium sulfate and concentrated under reduced pressure, and the residue thus obtained was purified by a silica gel column chromatography using a mixture of ethyl acetate and n-hexane of 1:2 to obtain 3.24 g of the title compound as an oil.

$^1$H NMR(200 MHz, CDCl$_3$) δ8.6 (1H, m), 7.8 (2H, m), 7.3 (1H, m), 4.1~3.6 (4H, m), 2.4 (2H, m)

Step 5) Synthesis of 3-cyano-3-(pyridin-2-yl)-4-(N-t-butoxycarbonyl)-pyrrolidine To a solution of 7.5 g of the compound obtained in Step 4 in 150 ml of THF was added 9.95 g of triphenylphosphine, and the resulting mixture was stirred for 1 hour. After the reaction was completed, the reaction solution was distilled under reduced pressure to remove THF therefrom, and 15 ml of xylene was added thereto. The resulting mixture was heated to reflux for 24 hours. After the completion of the reaction, reaction solution was distilled under reduced pressure to remove xylene and thereto were slowly added 150 ml of methanol and then 11.3 g of di-tert-butyl dicarbonate. The reaction product solution was concentrated under reduced pressure, and the residue thus obtained was purified by a silica gel column chromatography using a mixture of ethyl acetate and n-hexane of 1:4 to obtain 2.65 g of the title compound as an oil.

$^1$H NMR(200 MHz, CDCl$_3$) δ8.6 (1H, m), 7.8 (2H, m), 7.7 (1H, m), 7.3 (1H, m), 4.1~3.9 (4H, m), 3.7 (2H, m), 2.7~2.5 (2H, m), 1.5 (9H, s)

Step 6) Synthesis of 3-(N-t-butoxycarbonylaminomethyl)-3-(pyridin-2-yl)-1-(N-t-butoxycarbonyl)pyrrolidine A solution of 0.7 g of the compound obtained in Step 5 in 20 ml of methanol was hydrogenated for 2 hours in the presence of 70 mg of Raney nickel (10% w/w) under a hydrogen gas pressure of 60 psi. After the reaction was completed, the reaction solution was filtered with Celite® 545 and the filtrate was concentrated under reduced pressure. To the residue thus obtained were added 20 ml of methanol and then 0.84 g of di-t-butyl dicarbonate, and the resulting mixture was stirred for 2 hours. The reaction product solution was concentrated under reduced pressure, and the residue thus obtained was purified by a silica gel column chromatography using a mixture of ethyl acetate and n-hexane of 1:4 to obtain 0.55 g of the title compound as an oil.

$^1$H NMR(200 MHz, CDCl$_3$) δ8.5 (1H, m), 7.6 (1H, m), 7.2 (2H, m), 5.0 (1d, NH), 3.6~3.4 (6H, m), 2.2 (2H, m), 1.4 (9H, s), 1.3(9H, s)

Step 7) Synthesis of 3-aminomethyl-3-(pyridin-2-yl)pyrrolidine trihydrochloride

To solution of 1.1 g of the compound obtained in Step 6 dissolved in a small amount of methanol was added 10 ml of 20% HCl-methanol solution, and the resulting mixture was stirred at room temperature for 18 hours. The reaction mixture was filtered to obtain 0.65 mg of the title compound.

$^1$H NMR(200 MHz, D$_2$O) δ8.5 (1H, m), 7.9 (1H, m), 7.6 (1H, m), 4.0~3.2 (6H, m), 2.7~2.3 (2H, m)

Preparation 2: Synthesis of 3-aminomethyl-3-(pyridin-3-yl)pyrrolidine trihydrochloride The procedures of Preparation 1 were repeated except that (pyridyl-3-yl)acetonitrile was employed instead of (pyridyl-2-yl)acetonitrile to obtain the title compound.

Preparation 3: Synthesis of 3-aminomethyl-3-(pyridin-4-yl)pyrrolidine trihydrochloride The procedures of Preparation 1 were repeated except that (pyridyl-4-yl)acetonitrile was employed instead of (pyridyl-2-yl)acetonitrile to obtain the title compound.

Preparation 4: Synthesis of 3-amino-3-(pyridin-2-yl)pyrrolidine trihydrochloride Step 1) Synthesis of 3-carbamoyl-3-(pyridin-2-yl)-1-(N-t-butoxycarbonyl)pyrrolidine To a solution of 4.22 g of 3-cyano-3-(pyridin-2-yl)-1-(N-t-butoxycarbonyl)pyrrolidine obtained in Step 5 of Preparation 1 in 100 ml of xylene were added 6.7 g of manganese oxide and 5.56 g of silica gel. The resulting mixture was heated to reflux for 24 hours. After the reaction was completed, the reaction solution was filtered with Celite® 565 and the filtrate was concentrated under reduced pressure. The residue thus obtained was purified by a silica gel column chromatography using a mixture of ethyl acetate and n-hexane of 1:4 to obtain 3 g of the title compound as an oil.

$^1$H NMR(200 MHz, CDCl$_3$) δ8.6 (1H, m), 7.7 (1H, m), 7.3 (2H, m), 6.6 (1H, b, CONH$_2$), 5.7 (1H, b, CONH$_2$), 4.2~3.9 (2H, m), 3.5~3.3 (2H, m), 2.8~2.4 (2H, m), 1.5 (9H, s)

Step 2) Synthesis of 3-(N-methoxycarbonylamino)-3-(pyridin-2-yl)-1-(N-t-butoxycarbonyl)pyrrolidine To a solution of 1.1 g of the compound obtained in Step 1 in 100 ml of methanol was added 0.53 g of potassium hydroxide. After the resulting mixture was stirred for 5 minutes, 1.22 g of iodobenzene diacetate was added to the mixture at 0° C. The resulting mixture was heated to reflux for 1 hour. After the reaction was completed, the reaction solution was distilled under reduced pressure to remove methanol, thereto was added water. The resulting mixture was extracted with dichloromethane, and the organic phase was dried over anhydrous magnesium sulfate and concentrated under reduced pressure. The residue thus obtained was purified by a silica gel column chromatography using a mixture of ethyl acetate and n-hexane of 1:1 to obtain 1.1 g of the title compound as an oil.

$^1$H NMR(200 MHz, CDCl$_3$) δ8.5 (1H, m), 7.7 (1H, m), 7.4 (1H, m), 7.2 (1H, m), 5.6 (1H, b), 3.9 (2H, m), 3.6 (5H, m), 2.5 (2H, m), 1.5 (9H, s)

Step 3) Synthesis of 3-(N-t-butoxycarbonylamino)-3-(pyridin-2-yl)-1-(N-t-butoxycarbonyl)pyrrolidine A solution of 0.85 g of the compound obtained in Step 2 in 20 ml of concentrated HCl was heated to reflux for 24 hours. After the reaction was completed, the reaction solution was neutralized with 2N NaOH solution, and distilled under reduced pressure to remove water. To the residue were added a small amount of methanol and 1.44 g of di-t-butyl dicarbonate. The resulting mixture was stirred at room temperature for 1 day. The reaction mixture was concentrated under reduced pressure, and thereto was added water and extracted with ethyl acetate. The organic phase was dried over anhydrous magnesium sulfate and concentrated under reduced pressure. The residue thus obtained was purified by a silica gel column chromatography using a mixture of ethyl acetate and n-hexane of 1:2 to obtain 0.75 g of the title compound as an oil.

$^1$H NMR(200 MHz, CDCl$_3$) δ8.6 (1H, m), 7.7 (1H, m), 7.4 (1H, m), 7.2 (1H, m), 5.4 (1H, b), 3.8 (2H, m), 3.5 (5H, m), 2.5 (2H, m), 1.5 (9H, s), 1.3 (9H, s)

Step 4) Synthesis of 3-amino-3-(pyridin-2-yl)pyrrolidine trihydrochloride

To solution of 0.75 g of the compound obtained in Step 3 dissolved in a small amount of methanol was added 10 ml of 20% HCl-methanol solution, and the resulting mixture was stirred at room temperature for 1 day. The reaction mixture was concentrated under reduced pressure to obtain 0.55 g of the title compound.

$^1$H NMR(200 MHz, D$_2$O) δ8.5 (1H, m), 7.8 (1H, m), 7.5 (1H, m), 7.4 (1H, m), 4.0~3.7 (2H, m), 3.6 (2H, m), 2.6 (2H, m)

Preparation 5: Synthesis of 3-amino-3-(pyridin-3-yl)pyrrolidine trihydrochloride The procedures of Preparation 4 were repeated except that 3-cyano-3-(pyridin-3-yl)-1-(N-t-butoxycarbonyl)pyrrolidine obtained in the procedure of Preparation 2 was employed instead of 3-cyano-3-(pyridin-2-yl)-1-(N-t-butoxycarbonyl)pyrrolidine to obtain the title compound.

Preparation 6: Synthesis of 3-amino-3-(pyridin-4-yl)pyrrolidine trihydrochloride The procedures of Preparation 4 were repeated except that 3-cyano-3-(pyridin-4-yl)-1-(N-t-butoxycarbonyl)pyrrolidine obtained in the procedure of Preparation 3 was employed instead of 3-cyano-3-(pyridin-2-yl)-1-(N-t-butoxycarbonyl)pyrrolidine to obtain the title compound.

Preparation 7: Synthesis of 3-methylamino-3-(pyridin-2-yl)pyrrolidine trihydrochloride Step 1) Synthesis of 3-(N-methy-1N-t-butoxycarbonylamino)-3-(pyridin-2-yl)-1-(N-t-butoxycarbonyl)pyrrol 0.72 g of 60% NaH was added to the solution of 3.63 g of the compound obtained in Step 3 of Preparation 4 in 20 ml of DMF in a ice bath, the resulting mixture was stirred at room temperature for 3 hours. Then, to the reaction mixture was added a solution of 1.55 g of methyl iodide in 10 ml of DMF and the resulting mixture was stirred at 50° C. for 10 hours. After the reaction was completed, the reaction solution was poured in 100 ml of ice-water and extracted with ethyl acetate. The organic phase was dried over anhydrous magnesium sulfate and concentrated under reduced pressure. The residue thus obtained was purified by a silica gel column chromatography using a mixture of ethyl acetate and n-hexane of 1:2 to obtain 3.07 g of the title compound as an oil.

$^1$H NMR(200 MHz, CDCl$_3$) δ8.6 (1H, m), 7.7 (1H, m), 7.4 (1H, m), 7.2 (1H, m), 5.4 (1H, b), 3.8 (2H, m), 3.5 (5H, m), 2.5 (2H, m), 2.2 (3H, S), 1.5 (9H, s), 1.3(9H, s)

Step 2) Synthesis of 3-methylamino-3-(pyridin-2-yl)pyrrolidine trihydrochloride

To solution of 1.89 g of the compound obtained in Step 1 dissolved in a small amount of methanol was added 80 ml of 20% HCl-methanol solution, and the resulting mixture was stirred at room temperature for 1 day. The reaction mixture was concentrated under reduced pressure to obtain 2.62 g of the title compound.

$^1$H NMR(200 MHz, D$_2$O) (δ8.5 (1H, m), 7.8 (1H, m), 7.5 (1H, m), 7.4 (1H, m), 4.0~3.7 (2H, m), 3.6 (2H, m), 3.1 (3H, S), 2.6 (2H, m)

Preparation 8: Synthesis of 3-methylamino-3-(pyridin-3-yl)pyrrolidine trihydrochloride The procedures of Preparation 7 were repeated except that 3-(N-t-butoxycarbonylamino)-3-(pyridin-3-yl)-1-(N-t-butoxycarbonyl)pyrrolidine obtained in the procedure of step 3 of Preparation 4 was employed instead of 3-(N-t-butoxycarbonylamino)-3-(pyridin-2-yl)-1-(N-t-butoxycarbonyl)-pyrrolidine to obtain the title compound.

Preparation 9: Synthesis of 3-methylaminomethyl-3-(pyridin-4-yl)pyrrolidine trihydrochloride The procedures of Preparation 7 were repeated except that 3-(N-t-butoxycarbonylaminomethyl)-3-(pyridin-4-yl)-1-(N-t-butoxycarbonyl)pyrrolidine obtained in the procedure of step 6 of Preparation 1 was employed instead of 3-(N-t-butoxycarbonylamino)-3-(pyridin-2-yl)-1-(N-t-butoxycarbonyl)-pyrrolidine to obtain the title compound.

Preparation 10: Synthesis of 3-methyl-3-(pyridin-2-yl)pyrrolidine trihydrochloride Step 1) Synthesis of ethyl 3-(pyridin-2-yl)-2-butenoate To a solution of 25.57 ml of triethyl phosphonoacetate in 100 ml of toluene was slowly added 5 g of sodium hydride (60%) with stirring in an ice bath. The resulting mixture was stirred for 30 minutes and thereto was slowly added a solution of 10 g of 2-acetylpyridine dissolved in toluene. The resulting mixture was stirred at room temperature for 1 hour. After the reaction was completed, water was added. The resulting mixture was extracted with ethyl acetate, and the organic phase was dried over anhydrous magnesium sulfate and concentrated under reduced pressure. The residue thus obtained was purified by a silica gel column chromatography using a mixture of ethyl acetate and n-hexane of 1:4 to obtain 13.1 g of the title compound as a syrup.

¹H NMR(200 MHz, CDCl₃) δ8.6 (1H, m), 7.7 (1H, m), 7.2 (1H, m), 6.7 (1H, b), 4.2 (2H, q), 2.6 (3H, s), 1.3 (3H, t)

Step 2) Synthesis of ethyl 3-methyl-3-(pyridin-2-yl)-4-nitrobutanoate

A solution of 6 g of the compound obtained in Step 1, 3.36 ml of nitromethane and 4.26 ml of DBU dissolved in 120 ml of acetonitrile was heated to reflux for 36 hours. After the reaction was completed, the reaction solution was distilled under reduced pressure. The residue thus obtained was purified by a silica gel column chromatography using a mixture of ethyl acetate and n-hexane of 1:9 to obtain 1.8 g of the title compound as a syrup.

¹H NMR(200 MHz, CDCl₃) δ8.5 (1H, m), 7.7 (1H, m), 7.3 (1H, m), 7.2 (1H, m), 5.1 (2H, q), 4.1 (2H, q), 2.9 (2H, s), 1.6 (3H, s), 1.2 (3H, t)

Step 3) Synthesis of 3-methyl-3-(pyridin-2-yl)-4-pyrolidinone

A solution of 5.9 g of the compound obtained in Step 2 in 150 ml of ethanol was hydrogenated for 12 hours in the presence of 0.6 g of Raney nickel (10% w/w) under a hydrogen gas pressure of 60 psi. After the reaction was completed, the reaction solution was filtered with Celite® 545 and the filtrate was concentrated under reduced pressure. To the residue thus obtained was added 150 ml of toluene, and the resulting mixture was heated to reflux for 2 hours. The reaction product solution was concentrated under reduced pressure, and the residue thus obtained was purified by a silica gel column chromatography using a mixture of ethyl acetate and methanol of 9:1 to obtain 3.35 g of the title compound as a white solid.

Step 4) Synthesis of 1-(N-t-butoxycarbonyl)-3-methyl-3-(pyridin-2-yl)-pyrrolidine A solution of 3.35 g of the compound obtained in Step 3 in 85 ml of THF was sufficiently stirred in an ice bath under nitrogen blanket, and thereto was slowly added 1.44 g of lithium aluminium hydride. The resulting mixture was stirred at room temperature for 16 hours. After the reaction was completed, water was added, and the resulting mixture was filtered with Celite® 545 and distilled under reduced pressure to remove solvent. To the residue were added 60 ml of methanol and 6.22 g of di-t-butyl dicarbonate. The resulting mixture was stirred at room temperature for 3 hours. The reaction mixture was concentrated under reduced pressure, and thereto was added water and extracted with ethyl acetate. The organic phase was dried over anhydrous magnesium sulfate and concentrated under reduced pressure. The residue thus obtained was purified by a silica gel column chromatography using a mixture of ethyl acetate and n-hexane of 2:1 to obtain 2.4 g of the title compound as a colorless syrup.

¹H NMR(200 MHz, CDCl₃) δ8.5 (1H, m), 7.6 (1H, m), 7.3–7.0 (2H, m), 3.7–3.3 (4H, m), 2.4–1.9 (2H, m), 1.45 ((9H, s), 1.4 (3H, s)

Step 5) Synthesis of 3-methyl-3-(pyridin-2-yl)pyrrolidine trihydrochloride

To solution of 0.95 g of the compound obtained in Step 4 dissolved in a small amount of methanol was added 16 ml of 20% HCl-methanol solution, and the resulting mixture was stirred at room temperature for 12 hours. The reaction solution was filtered to obtain 0.6 g of the title compound.

¹H NMR(200 MHz, D₂O) δ8.6 (1H, m), 8.5 (1H, m), 7.9 (2H, m), 3.5 (4H, m), 2.4 (2H, m), 1.5 (3H, s)

Preparation 11: Synthesis of 3-methyl-3-(pyridin-3-yl)pyrrolidine trihydrochloride The procedures of Preparation 10 were repeated except that 3-acetylpyridine was employed instead of 2-acetylpyridine to obtain the title compound.

Preparation 12: Synthesis of 3-methyl-3-(pyridin-4-yl)pyrrolidine trihydrochloride The procedures of Preparation 10 were repeated except that 4-acetylpyridine was employed instead of 2-acetylpyridine to obtain the title compound.

Preparation 13: Synthesis of 3-(pyridin-4-yl)pyrrolidine trihydrochloride

The procedures of Preparation 10 were repeated except that 4-formylpyridine was employed instead of 2-acetylpyridine to obtain the title compound.

Preparation 14: Synthesis of 3-aminoethyl-3-(pyridin-2-yl)pyrrolidine trihydrochloride Step 1) Synthesis of 3-aminoethyl-3-(pyridin-2-yl)-4-(N-t-butoxycarbonyl)-pyrrolidine To the solution of 2.73 g of 3-cyano-3-(pyridin-2-yl)-4-(N-t-butoxycarbonyl)pyrrolidine obtained in Step 5 of Preparation 1 in 50 ml of THF in a dry ice-acetone bath, 5 ml of 3.0M solution of methylmagnesiumchloride in THF was added dropwise slowly at −30° C. and the resulting solution was stirred effectively at the same temperature. After the reaction was completed, the temperature of reaction mixture was raised to room temperature and then, the aqueous solution of ammonium chloride was added, stirred well for 1 hour and extracted with ethyl acetate. The organic phase was dried over anhydrous magnesium sulfate and concentrated under reduced pressure. To solution of the residue in 100 ml of methanol, 100 ml of 28% ammonia water was added in sealed flask and stirred for 10 hours. 1.15 g of sodiumborocyanohydride was added to the resulting reaction mixture and stirred for 7 hours, then concentrated under reduced pressure. The residue thus obtained was purified by a silica gel column chromatography using a mixture of ethyl acetate and n-hexane of 5:1 to obtain 1.82 g of the title compound as an oil.

Step 2) Synthesis of 3-aminoethyl-3-(pyridin-2-yl)pyrrolidine trihydrochloride

To solution of 1.46 g of the compound obtained in Step 1 dissolved in a small amount of methanol was added 16 ml of 20% HCl-methanol solution, and the resulting mixture was stirred at room temperature for 12 hours. The reaction solution was filtered to obtain 1.41 g of the title compound.

¹H NMR(200 MHz, D₂O) δ8.6 (1H, m), 8.5 (1H, m), 7.9 (2H, m), 4.3 (1H, m), 3.7 (4H, m), 2.4 (2H, m), 1.7 (3H, d)

EXAMPLE 1

Synthesis of 1-cyclopropyl-6,8-difluoro-7-[{3-aminomethyl-3-(pyridin-2-yl)pyrrolidin}-1-yl]-4-oxo-1,4-dihydroquinolin-3-carboxylic acid (Compound 1)

283 mg of 1-cyclopropyl-6,7,8-trifluoro-4-oxo-1,4-dihydroquinolin-3-carboxylic acid, 315 mg of 3-aminomethyl-3-(pyridin-2-yl)pyrrolidine trihydrochloride obtained in Preparation 1, and 200 mg of diazabicyclo[5.4.0]undec-7-ene were added to 10 ml of acetonitrile, and the resulting mixture was refluxed for 6 hours, cooled, filtered and dried to give 334 mg of the title compound as a light-yellow solid.

¹H NMR(200 MHz, CDCl₃—CD₃OD): δ8.80 (1H, m), 8.70 (1H, m), 8.00 (1H, m), 7.68 (2H, m), 7.13 (1H, m), 4.5 (2H, m), 4.10 (1H, m), 3.70–3.90 (4H, m), 2.60 (2H, m), 1.02 (4H, m)

Elemental Analysis (C$_{23}$H$_{22}$N$_4$O$_3$F$_2$) Measured(%): C: 62.61, H: 5.18, N: 12.54. Calculated(%): C: 62.72, H: 5.03, N: 12.72.

EXAMPLE 2

Synthesis of 1-cyclopropyl-6-fluoro-8-chloro-7-[{3-aminomethyl-3-(pyridin-2-yl)pyrrolidin}-1-yl]-4-oxo-1,4-dihydroquinolin-3-carboxylic acid (Compound 2)

The procedure of Example 1 was repeated except that 298 mg of 1-cyclopropyl-6,7-difluoro-8-chloro-4-oxo-1,4-dihydroquinolin-3-carboxylic acid and 315 mg of 3-aminomethyl-3-(pyridin-2-yl)pyrrolidine trihydrochloride obtained in Preparation 1 were used, to give 406 mg of the title compound as a white solid.

$^1$H NMR(200 MHz, CDCl$_3$—CD$_3$OD): δ8.82 (1H, m), 8.71 (1H, m), 8.00 (1H, d), 7.75 (1H, m), 7.37 (1H, m), 7.30 (1H, m), 4.5 (2H, m), 4.10 (1H, m), 3.70–3.90 (4H, m), 2.60 (2H, m), 1.12 (4H, m)

Elemental Analysis (C$_{23}$H$_{22}$N$_4$O$_3$FCl) Measured(%): C: 60.41, H: 4.81, N: 12.30. Calculated(%): C: 60.46, H: 4.85, N: 12.26.

EXAMPLE 3

Synthesis of 1-cyclopropyl-6-fluoro-8-methoxy-7-[{3-aminomethyl-3-(pyridin-2-yl)pyrrolidin}-1-yl]-4-oxo-1,4-dihydroquinolin-3-carboxylic acid (Compound 3)

The procedure of Example 1 was repeated except that 293 mg of 1-cyclopropyl-6,7-difluoro-8-methoxy-4-oxo-1,4-dihydroquinolin-3-carboxylic acid, and 315 mg of 3-aminomethyl-3-(pyridin-2-yl)pyrrolidine. trihydrochloride obtained in Preparation 1 were used, to give 382 mg of the title compound.

Elemental Analysis (C$_{24}$H$_{25}$N$_4$O$_4$F) Measured(%): C: 63.66, H: 5.59, N: 12.37. Calculated(%): C: 63.71, H: 5.57, N: 12.38.

EXAMPLE 4

Synthesis of 1-cyclopropyl-5-amino-6,8-difluoro-7-[{3-aminomethyl-3-(pyridin-2-yl)pyrrolidin}-1-yl]-4-oxo-1,4-dihydroquinolin-3-carboxylic acid (Compound 4)

The procedure of Example 1 was repeated except that 295 mg of 1-cyclopropyl-5-amino-6,7,8-trifluoro-4-oxo-1,4-dihydroquinolin-3-carboxylic acid, and 315 mg of 3-aminomethyl-3-(pyridin-2-yl)pyrrolidine trihydrochloride obtained in Preparation 1 were used, to give 396 mg of the title compound as a yellow solid.

Elemental Analysis (C$_{23}$H$_{23}$N$_5$O$_3$F$_2$) Measured(%): C: 60.71, H: 5.06, N: 15.41. Calculated(%): C: 60.65, H: 5.09, N: 15.38.

EXAMPLE 5

Synthesis of 1-cyclopropyl-6-fluoro-7-[{3-aminomethyl-3-(pyridin-2-yl)pyrrolidin}-1-yl]-4-oxo-1,4-dihydroquinolin-3-carboxylic acid (Compound 5)

The procedure of Example 1 was repeated except that 263 mg of 1-cyclopropyl-6,7-difluoro-4-oxo-1,4-dihydroquinolin-3-carboxylic acid and 315 mg of 3-aminomethyl-3-(pyridin-2-yl)pyrrolidine trihydrochloride obtained in Preparation 1 were used, to give 361 mg of the title compound as a white solid.

Elemental Analysis (C$_{23}$H$_{23}$N$_4$O$_3$F) Measured(%): C: 65.41, H: 5.46, N: 13.21. Calculated(%): C: 65.39, H: 5.49, N: 13.26.

EXAMPLE 6

Synthesis of 9-fluoro-2,3-dihydro-3-(S)-methyl-10-[{3-aminomethyl-3-(pyridin-2-yl)pyrrolidin}-1-yl]-7-oxo-7H-pyrido[1.2.3-de]-1,4-benzoxazine-6-carboxylic acid (Compound 6)

The procedure of Example 1 was repeated except that 287 mg of 9,10-difluoro-2,3-dihydro-3-(S)-methyl-7-oxo-7H-pyrido[1.2.3-de]-1,4-benzoxazine-6-carboxylic acid, and 315 mg of 3-aminomethyl-3-(pyridin-2-yl)pyrrolidine trihydrochloride obtained in Preparation 1 were used, to give 386 mg of the title compound.

Elemental Analysis (C$_{23}$H$_{23}$N$_4$O$_3$F) Measured(%): C: 63.06, H: 5.26, N: 12.81. Calculated(%): C: 63.00, H: 5.29, N: 12.78.

EXAMPLE 7

Synthesis of 1-cyclopropyl-6-fluoro-7-[{3-aminomethyl-3-(pyridin-2-yl)pyrrolidin}-1-yl]-4-oxo-1,4-dihydro-1,8-naphthylidin-3-carboxylic acid (Compound 7)

The procedure of Example 1 was repeated except that 264 mg of 1-cyclopropyl-6,7-difluoro-4-oxo-1,4-dihydro-1,8-naphthylidin-3-carboxylic acid, and 315 mg of 3-aminomethyl-3-(pyridin-2-yl)pyrrolidine trihydrochloride obtained in Preparation 1 were used, to give 393 mg of the title compound.

$^1$H NMR(200 MHz, CDCl$_3$—CD$_3$OD): δ8.48 (1H, m), 8.21 (1H, s), 7.80 (1H, m), 7.58 (2H, m), 7.32 (1H, m), 4.00 (1H, m), 3.80 (3H, m), 3.31 (2H, m), 2.20–2.40 (3H, m), 11.13 (2H, m), 0.82 (2H, m)

Elemental Analysis (C$_{22}$H$_{22}$N$_5$O$_3$F) Measured(%): C: 62.45, H: 5.21, N: 15.51. Calculated(%): C: 62.40, H: 5.24, N: 16.54.

EXAMPLE 8

Synthesis of 1-(2,4-difluorophenyl)-6-fluoro-7-[{3-aminomethyl-3-(pyridin-2-yl)pyrrolidin}-1-yl]-4-oxo-1,4-dihydro-1,8-naphthylidin-3-carboxylic acid (Compound 8)

The procedure of Example 1 was repeated except that 334 mg of 1-(2,4-difluorophenyl)-6,7-difluoro-4-oxo-1,4-dihydro-1,8-naphthylidin-3-carboxylic acid and 315 mg of 3-aminomethyl-3-(pyridin-2-yl)pyrrolidine trihydrochloride obtained in Preparation 1 were used, to give 433 mg of the title compound.

Elemental Analysis (C$_{25}$H$_{20}$N$_5$O$_3$F$_3$) Measured(%): C: 60.63, H: 4.06, N: 14.15. Calculated(%): C: 60.60, H: 4.07, N: 14.14.

EXAMPLE 9

Synthesis of 1-cyclopropyl-6,8-difluoro-7-[{3-methylamino-3-(pyridin-2-yl)pyrrolidin}-1-yl]-4-oxo-1,4-dihydroquinolin-3-carboxylic acid (Compound 9)

The procedure of Example 1 was repeated except that 280 mg of 1-cyclopropyl-6,7,8-trifluoro-4-oxo-1,4-dihydroquinolin-3-carboxylic acid, and 315 mg of 3-methylamino-3-(pyridin-2-yl)pyrrolidine hydrochloride obtained in Preparation 7 were employed, to give 340 mg of the title compound.

Elemental Analysis ($C_{23}H_{22}N_4O_3F_2$) Measured(%): C: 62.61, H: 5.18, N: 12.54. Calculated(%): C: 62.72, H: 5.03, N: 12.72.

EXAMPLE 10

Synthesis of 1-cyclopropyl-6-fluoro-8-methoxy-7-[{3-aminomethyl-3-(pyridin-4-yl)pyrrolidin}-1-yl]-4-oxo-1,4-dihydroquinolin-3-carboxylic acid (Compound 10)

The procedure of Example 1 was repeated except that 295 mg of 1-cyclopropyl-6,7-difluoro-8-methoxy-4-oxo-1,4-dihydroquinolin-3-carboxylic acid, and 315 mg of 3-aminomethyl-3-(pyridin-4-yl)pyrrolidine hydrochloride obtained in Preparation 3 were employed, to give 401 mg of the title compound as a white solid.

Elemental Analysis ($C_{24}H_{25}N_4O_4F$) Measured(%): C: 63.68, H: 5.57, N: 12.41. Calculated(%): C: 63.71, H: 5.57, N: 12.38.

EXAMPLE 11

Synthesis of 1-cyclopropyl-6-fluoro-8-methoxy-7-[{3-amino-3-(pyridin-4-yl)pyrrolidin}-1-yl]-4-oxo-1,4-dihydroquinolin-3-carboxylic acid (Compound 10)

The procedure of Example 1 was repeated except that 295 mg of 1-cyclopropyl-6,7-difluoro-8-methoxy-4-oxo-1,4-dihydroquinolin-3-carboxylic acid, and 315 mg of 3-amino-3-(pyridin-4-yl)pyrrolidine hydrochloride obtained in Preparation 6 were employed, to give 407 mg of the title compound as a white solid.

$^1$H NMR(200 MHz, $CDCl_3$—$CD_3OD$): δ8.66 (1H, s), 8.62 (1H, t), 7.97 (1H, d), 7.78 (1H, m), 7.55 (2H, d), 7.27 (1H, m), 4.29 (4H, m), 3.66 (1H, m), 2.64 (4H, m), 2.26 (1H, m), 1.26 (2H, m), 1.07 (2H, m)

Elemental Analysis ($C_{23}H_{23}N_4O_4F$) Measured(%): C: 63.05, H: 5.31, N: 12.75. Calculated(%): C: 63.00, H: 5.29, N: 12.78.

EXAMPLE 12

Synthesis of 1-cyclopropyl-5-amino-6,8-difluoro-7-[{3-aminomethyl-3-(pyridin-4-yl)pyrrolidin}-1-yl]-4-oxo-1,4-dihydroquinolin-3-carboxylic acid (Compound 12)

The procedure of Example 1 was repeated except that 298 mg of 1-cyclopropyl-5-amino-6,7,8-trifluoro-4-oxo-1,4-dihydroquinolin-3-carboxylic acid, and 315 mg of 3-aminomethyl-3-(pyridin-4-yl)pyrrolidine hydrochloride obtained in Preparation 3 were employed, to give 401 mg of the title compound.

Elemental Analysis ($C_{23}H_{23}N_5O_3F_2$) Measured(%): C: 60.67, H: 5.12, N: 15.35. Calculated(%): C: 60.65, H: 5.09, N: 15.38.

EXAMPLE 13

Synthesis of 9-fluoro-2,3-dihydro-3-(S)-methyl-10-[{3-aminomethyl-3-(pyridin-4-yl)pyrrolidin}-1-yl]-7-oxo-7H-pyrido[1.2.3-de]-1,4-benzoxazine-6-carboxylic acid (Compound 13)

The procedure of Example 1 was repeated except that 287 mg of 9,10-difluoro-2,3-dihydro-3-(S)-methyl-7-oxo-7H-pyrido[1.2.3-de]-1,4-benzoxazine-6-carboxylic acid, and 300 mg of 3-amino-3-(pyridin-4-yl)pyrrolidine hydrochloride obtained in Preparation 6 were employed, to give 375 mg of the title compound.

Elemental Analysis ($C_{22}H_{21}N_4O_4F$) Measured(%): C: 62.24, H: 5.01, N: 13.20. Calculated(%): C: 62.26, H: 4.99, N: 13.20.

EXAMPLE 14

Synthesis of 1-cyclopropyl-6-fluoro-7-[{3-amino-3-(pyridin-3-yl)pyrrolidin}-1-yl]-4-oxo-1,4-dihydro-1,8-naphthylidin-3-carboxylic acid (Compound 14)

The procedure of Example 1 was repeated except that 282 mg of 1-cyclopropyl-6-fluoro-7-chloro-4-oxo-1,4-dihydro-1,8-naphthylidin-3-carboxylic acid and 300 mg of 3-amino-3-(pyridin-3-yl)pyrrolidine hydrochloride obtained in Preparation 5 were employed, to give 382 mg of the title compound.

Elemental Analysis ($C_{21}H_{20}N_5O_3F$) Measured(%): C: 61.65, H: 4.89, N: 17.14. Calculated(%): C: 61.61, H: 4.92, N: 11.11.

EXAMPLE 15

Synthesis of 1-cyclopropyl-6-fluoro-7-[{3-aminomethyl-3-(pyridin-3-yl)pyrrolidin}-1-yl]-4-oxo-1,4-dihydroquinolin-3-carboxylic acid (Compound 15)

The procedure of Example 1 was repeated except that 295 mg of 1-cyclopropyl-6,7-difluoro-4-oxo-1,4-dihydroquinolin-3-carboxylic acid and 315 mg of 3-aminomethyl-3-(pyridin-3-yl)pyrrolidine hydrochloride obtained in Preparation 2 were employed, to give 367 mg of the title compound.

Elemental Analysis ($C_{23}H_{23}N_4O_3F$) Measured(%): C: 65.39, H: 5.51, N: 13.31. Calculated(%): C: 65.39, H: 5.49, N: 13.26.

EXAMPLE 16

Synthesis of 1-cyclopropyl-6,8-difluoro-7-[{3-amino-3-(pyridin-4-yl)pyrrolidin}-1-yl]-4-oxo-1,4-dihydroquinolin-3-carboxylic acid (Compound 16)

The procedure of Example 1 was repeated except that 295 mg of 1-cyclopropyl-6,7,8-trifluoro-4-oxo-1,4-dihydroquinolin-3-carboxylic acid and 300 mg of 3-amino-3-(pyridin-4-yl)pyrrolidine hydrochloride obtained in Preparation 6 were employed, to give 367 mg of the title compound.

Elemental Analysis ($C_{22}H_{20}N_4O_3F_2$) Measured(%): C: 61.98, H: 4.71, N: 13.11. Calculated(%): C: 61.97, H: 4.73, N: 13.14.

EXAMPLE 17

Synthesis of 1-cyclopropyl-6-fluoro-8-methoxy-7-[{3-methylaminomethyl-3-(pyridin-4-yl)pyrrolidin}-1-yl]-4-oxo-1,4-dihydroquinolin-3-carboxylic acid (Compound 17)

The procedure of Example 1 was repeated except that 295 mg of 1-cyclopropyl-6,7-difluoro-8-methoxy-4-oxo-1,4-dihydroquinolin-3-carboxylic acid and 320 mg of 3-methylaminomethyl-3-(pyridin-4-yl)pyrrolidine hydrochloride obtained in Preparation 9 were employed, to give 376 mg of the title compound as a white solid.
Elemental Analysis ($C_{24}H_{25}N_4O_4F$) Measured(%): C: 64.41, H: 5.81, N: 12.00. Calculated(%): C: 64.37, H: 5.83, N: 12.01.

EXAMPLE 18

Synthesis of 1-cyclopropyl-6-fluoro-8-methoxy-7-[{3-methylamino-3-(pyridin-3-yl)pyrrolidin}-1-yl]-4-oxo-1,4-dihydroquinolin-3-carboxylic acid (Compound 18)

The procedure of Example 1 was repeated except that 295 mg of 1-cyclopropyl-6,7-difluoro-8-methoxy-4-oxo-1,4-dihydroquinolin-3-carboxylic acid and 315 mg of 3-methylamino-3-(pyridin-3-yl)pyrrolidine hydrochloride obtained in Preparation 8 were employed, to give 381 mg of the title compound as a white solid.
Elemental Analysis ($C_{24}H_{25}N_4O_4F$) Measured(%): C: 63.75, H: 5.59, N: 12.42. Calculated(%): C: 63.71, H: 5.57, N: 12.38.

EXAMPLE 19

Synthesis of 1-cyclopropyl-5-amino-6,8-difluoro-7-[{3-aminomethyl-3-(pyridin-3-yl)pyrrolidin}-1-yl]-4-oxo-1,4-dihydroquinolin-3-carboxylic acid (Compound 19)

The procedure of Example 1 was repeated except that 298 mg of 1-cyclopropyl-5-amino-6,7,8-trifluoro-4-oxo-1,4-dihydroquinolin-3-carboxylic acid and 315 mg of 3-aminomethyl-3-(pyridin-3-yl)pyrrolidine hydrochloride obtained in Preparation 2 were employed, to give 370 mg of the title compound.
Elemental Analysis ($C_{23}H_{23}N_5O_3F_2$) Measured(%): C: 60.61, H: 5.11, N: 15.39. Calculated(%): C: 60.65, H: 5.09, N: 15.38.

EXAMPLE 20

Synthesis of 9-fluoro-2,3-dihydro-3-(S)-methyl-10-[{3-methylamino-3-(pyridin-3-yl)pyrrolidin}-1-yl]-7-oxo-7H-pyrido[1.2.3-de]-1,4-benzoxazine-6-carboxylic acid (Compound 20)

The procedure of Example 1 was repeated except that 281 mg of 9,10-difluoro-2,3-dihydro-3-(S)-methyl-7-oxo-7H-pyrido[1.2.3-de]-1,4-benzoxazine-6-carboxylic acid, and 315 mg of 3-methylamino-3-(pyridin-3-yl)pyrrolidine hydrochloride obtained in Preparation 8 were employed, to give 391 mg of the title compound.
Elemental Analysis ($C_{23}H_{23}N_4O_4F$) Measured(%): C: 63.02, H: 5.30, N: 12.74. Calculated(%): C: 63.00, H: 5.29, N: 12.78.

EXAMPLE 21

Synthesis of 1-(2-(S)-fluorocyclopropyl)-6-fluoro-8-methoxy-7-[{3-aminomethyl-3-(pyridin-4-yl)pyrrolidin}-1-yl]-4-oxo-1,4-dihydroquinolin-3-carboxylic acid (Compound 21)

The procedure of Example 1 was repeated except that 313 mg of 1-(2-(S)-fluorocyclopropyl)-6,7-difluoro-8-methoxy-4-oxo-1,4-dihydroquinolin-3-carboxylic acid and 141 mg of 3-aminomethyl-3-(pyridin-4-yl) pyrrolidine obtained in Preparation 3 were employed, to give 417 mg of the title compound.
Elemental Analysis ($C_{23}H_{22}N_4O_4F$) Measured(%): C: 60.56, H: 4.83, N: 12.31. Calculated(%): C: 60.52, H: 4.86, N: 12.27.

EXAMPLE 22

Synthesis of 1-cyclopropyl-6-fluoro-8-methoxy-7-[{3-methyl-3-(pyridin-3-yl)pyrrolidin}-1-yl]-4-oxo-1,4-dihydro-quinolin-3-carboxylic acid (Compound 22)

The procedure of Example 1 was repeated except that 295 mg of 1-cyclopropyl-6,7-difluoro-8-methoxy-4-oxo-1,4-dihydroquinolin-3-carboxylic acid and 230 mg of 3-methyl-3-(pyridin-3-yl)pyrrolidine obtained in Preparation 11 were employed, to give 378 mg of the title compound.
Elemental Analysis ($C_{21}H_{20}N_5O_3F$) Measured(%): C: 61.58, H: 4.91, N: 17.11. Calculated(%): C: 61.61, H: 4.92, N: 17.11.

EXAMPLE 23

Synthesis of 1-cyclopropyl-5-methyl-6-fluoro-7-[{3-amino-3-(pyridin-4-yl)pyrrolidin}-1-yl]-4-oxo-1,4-dihydro-1,8-naphthylidin-3-carboxylic acid (Compound 23)

The procedure of Example 1 was repeated except that 291 mg of 1-cyclopropyl-5-methyl-6-fluoro-7-chloro-4-oxo-1,4-dihydro-1,8-naphthylidin-3-carboxylic acid and 300 mg of 3-amino-3-(pyridin-4-yl)pyrrolidine hydrochloride obtained in Preparation 6 were employed, to give 423 mg of the title compound.
Elemental Analysis ($C_{22}H_{22}N_5O_3F$) Measured(%): C: 62.35, H: 5.21, N: 16.51. Calculated(%): C: 62.40, H: 5.24, N: 16.54.

EXAMPLE 24

Synthesis of 1-t-butyl-6-fluoro-7-[{3-amino-3-(pyridin-4-yl)pyrrolidin}-1-yl]-4-oxo-1,4-dihydro-1,8-naphthylidin-3-carboxylic acid (Compound 24)

The procedure of Example 1 was repeated except that 291 mg of 1-t-butyl-6-fluoro-7-chloro-4-oxo-1,4-dihydro-1,8-naphthylidin-3-carboxylic acid and 300 mg of 3-amino-3-(pyridin-4-yl)pyrrolidine hydrochloride obtained in Preparation 6 were employed, to give 423 mg of the title compound.
Elemental Analysis ($C_{22}H_{24}N_5O_3F$) Measured(%): C: 62.08, H: 5.71, N: 16.41. Calculated(%): C: 62. 11, H: 5.69, N: 16.46.

EXAMPLE 25

Synthesis of 1-cyclopropyl-6-fluoro-8-methoxy-7-[{3-(pyridin-4-yl)pyrrolidin}-1-yl]-4-oxo-1,4-dihydroquinolin-3-carboxylic acid (Compound 25)

The procedure of Example 1 was repeated except that 295 mg of 1-cyclopropyl-6,7-difluoro-8-methoxy-4-oxo-1,4-dihydroquinolin-3-carboxylic acid and 230 mg of 3-(pyridin-4-yl)pyrrolidine hydrochloride obtained in Preparation 14 were employed, to give 347 mg of the title compound.

Elemental Analysis ($C_{23}H_{22}N_3O_4F$) Measured(%): C: 65.18, H: 5.21, N: 9.91. Calculated(%): C: 65.24, H: 5.24, N: 9.92.

EXAMPLE 26

Synthesis of 1-cyclopropyl-6-fluoro-8-methoxy-7-[{3-methyl-3-(pyridin-4-yl)pyrrolidin}-1-yl]-4-oxo-1,4-dihydroquinolin-3-carboxylic acid (Compound 26)

The procedure of Example 1 was repeated except that 295 mg of 1-cyclopropyl-6,7-difluoro-8-methoxy-4-oxo-1,4-dihydroquinolin-3-carboxylic acid and 230 mg of 3-methyl-3-(pyridin-4-yl)pyrrolidine hydrochloride obtained in Preparation 12 were employed, to give 351 mg of the title compound.

Elemental Analysis ($C_{24}H_{24}N_3O_4F$) Measured(%): C: 65.88, H: 5.51, N: 9.61. Calculated(%): C: 65.89, H: 5.53, N: 9.63.

EXAMPLE 27

Synthesis of 1-cyclopropyl-6-fluoro-8-methoxy-7-[{3-methyl-3-(pyridin-2-yl)pyrrolidin}-1-yl]-4-oxo-1,4-dihydroquinolin-3-carboxylic acid (Compound 27)

The procedure of Example 1 was repeated except that 295 mg of 1-cyclopropyl-6,7-difluoro-8-methoxy-4-oxo-1,4-dihydroquinolin-3-carboxylic acid and 230 mg of 3-methyl-3-(pyridin-2-yl)pyrrolidine hydrochloride obtained in Preparation 10 were employed, to give 365 mg of the title compound.

Elemental Analysis ($C_{24}H_{24}N_3O_4F$) Measured(%): C: 65.88, H: 5.51, N: 9.57. Calculated(%): C: 65.89, H: 5.53, N: 9.61.

EXAMPLE 28

Synthesis of 1-cyclopropyl-6-fluoro-8-methoxy-7-[{3-(1-aminoethyl)-3-(pyridin-2-yl)pyrrolidin}-1-yl]-4-oxo-1,4-dihydroquinolin-3-carboxylic acid (Compound 28)

The procedure of Example 1 was repeated except that 295 mg of 1-cyclopropyl-6,7-difluoro-8-methoxy-4-oxo-1,4-dihydroquinolin-3-carboxylic acid and 340 mg of 3-(1'-aminoethyl)-3-(pyridin-2-yl)pyrrolidine hydrochloride obtained in Preparation 15 were employed, to give 415 mg of the title compound.

Elemental Analysis ($C_{25}H_{27}N_4O_4F$) Measured(%): C: 64.38, H: 5.81, N: 12.05. Calculated(%): C: 64.37, H: 5.83, N: 12.01.

Test 1. Antibacterial Activity In Vitro

In order to measure antibacterial activities of the compounds of the present invention, minimal inhibitory concentrations (MIC, µg/ml) of representative compounds against standard strains were determined and compared-with those of ciprofloxacin and sparfloxacin, which were used as control compounds.

The MIC values were determined employing a two-fold dilution method and Muller Hinton agar medium. Each of the Hoechst 345 standard strains having the concentration of $10^7$CFU (colony forming unit)/ml was inoculated onto the medium, and incubated at 37° C. for 18 hours.

The results of the MIC tests are shown in Table I.

TABLE I

| standard test strains | Compound 3 | Compound 11 | Ciprofloxacin | Sparfloxacin |
|---|---|---|---|---|
| Streptococcus pyogenes A 308 | 0.013 | 0.025 | 3.125 | 0.391 |
| Streptococcus pyogenes A 77 | 0.007 | 0.013 | 0.781 | 0.195 |
| Streptococcus faecium MD 8b | 0.007 | 0.025 | 0.391 | 0.391 |
| Staphylococcus aureus SG 511 | 0.007 | 0.013 | 0.195 | 0.098 |
| Staphylococcus aureus 285 | 0.013 | 0.013 | 0.781 | 0.049 |
| Staphylococcus aureus 503 | 0.007 | 0.007 | 0.391 | 0.049 |
| Escherchia coli 078 | <0.002 | <0.002 | 0.004 | 0.004 |
| Escherchia coli DC0 | 0.049 | 0.049 | 0.195 | 0.195 |
| Escherchia coli DC2 | 0.013 | 0.013 | 0.049 | 0.025 |
| Escherchia coli TEM | 0.007 | 0.007 | 0.007 | 0.013 |
| Escherchia coli 1507E | 0.007 | 0.013 | 0.007 | 0.025 |
| Pseudomonas aeruginosa 9027 | 0.195 | 0.195 | 0.195 | 0.781 |
| Pseudomonas aeruginosa 1592E | 0.195 | 0.195 | 0.195 | 0.781 |
| Pseudomonas aeruginosa 1771 | 0.098 | 0.195 | 0.195 | 0.781 |
| Pseudomonas aeruginosa 1771M | 0.098 | 0.098 | 0.049 | 0.195 |
| Salmonella typhymurium | 0.007 | 0.007 | 0.007 | 0.007 |
| Klebsiella oxytoca 1082E | <0.002 | 0.002 | <0.002 | <0.002 |
| Klebsiella oxytoca 1522E | 0.013 | 0.013 | 0.013 | 0.025 |
| Enterobacter cloacae P99 | 0.007 | 0.004 | 0.007 | 0.007 |
| Enterobacter cloacae 1321E | <0.002 | 0.002 | <0.002 | 0.004 | note:
ciprofloxacin: 1-cyclopropyl-6-fluoro-7-(piperazin-1-yl)-4-oxoquinoline-3-carboxylic acid
sparfloxacin: 1-cyclopropyl-5-amino-6,8-difluoro-7-(3,5-dimethylpiperazin-1-yl)-4-oxoquinoline-3-carboxylic acid

Test 2. Selectivity Index

Selectivity indexes of the compounds of the present invention and control compounds were measured using gyrase purified from of *E. coli* and calf thymus topoisomerase II obtained from Topogen. Co.

The selectivity index (S.I.) was calculated by the equation 1.

$$S.I. = \frac{IC_{100, Topo\ II}}{IC_{100, Gyrase}} \quad \text{(Eq. 1)}$$

wherein, $IC_{100,\ Topo\ II}$ is the concentration of a compound to inhibit the enzyme activity of topoisomerase II and $IC_{100,\ Gyrase}$ is the concentration of a compound to inhibit the enzyme activity of gyrase of *E. coli*.

The results are shown in Table II.

TABLE II

|  | $IC_{100,\ Topo\ II}$ (μg/ml) | $IC_{100,\ Gyrase}$ (μg/ml) | S.I. |
|---|---|---|---|
| Compound 3 | 1,000 | 0.2 | 5,000 |
| Compound 11 | 1,000 | 0.4 | 2,500 |
| Ciprofloxacin | 500 | 0.5 | 1,000 |
| Sparfloxacin | 500 | 1.0 | 500 |

As can be seen from Tables I and II, the quinolone carboxylic acid derivatives of the present invention generally exhibit superior antibacterial activities against both Gram-positive and Gram-negative bacteria and much lower toxicities as compared with the control compounds.

While the embodiments of the subject invention have been described and illustrated, it is obvious that various changes and modifications can be made therein without departing from the spirit of the present invention which should be limited only by the scope of the appended claims.

What is claimed is:

1. A quinolone carboxylic acid derivative of formula (I) or a pharmaceutically acceptable salt thereof:

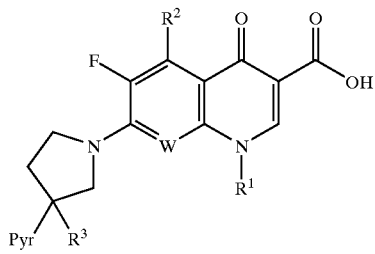

wherein,
$R^1$ is a $C_{1-4}$ alkyl group, or a phenyl or $C_{3-6}$ cycloalkyl group optionally substituted with one or more halogens;
$R^2$ is H, amino or $C_{1-4}$ alkyl group;
$R^3$ is a, $C_{1-4}$ alkyl group, or amino, aminomethyl or aminoethyl group optionally substituted with one $C_{1-4}$ alkyl radical;
W is N, CH or CY (Y is halogen, or $C_{1-4}$ alkyl or $C_{1-4}$ alkoxy group optionally substituted with one or more halogens); and
Pyr represents 2-, 3- or 4-pyridyl.

2. The quinolone carboxylic acid derivative of claim 1, wherein $R^1$ is ethyl, t-butyl, cyclopropyl, 2,4-difluorophenyl or 2-(S)-fluorocyclopropyl group; $R^2$ is hydrogen, amino or methyl group; $R^3$ is hydrogen, methyl, amino, methylamino, aminomethyl, methylaminomethyl or 1-aminoethyl; and W is N, CH, CF, CCl, $CCH_3$, $COCH_3$, $COCH_2F$ or $COCHF_2$.

* * * * *